United States Patent [19]

Withers et al.

[11] Patent Number: 4,544,785

[45] Date of Patent: Oct. 1, 1985

[54] METHANE CONVERSION

[75] Inventors: Howard P. Withers, Pottstown; John A. Sofranko, Malvern, both of Pa.

[73] Assignee: Atlantic Richfield Company, Los Angeles, Calif.

[21] Appl. No.: 600,659

[22] Filed: Apr. 16, 1984

[51] Int. Cl.[4] ............................................. C07C 2/00
[52] U.S. Cl. .................................... 585/500; 585/415; 585/417; 585/541; 585/654; 585/656; 585/658; 585/700; 585/943
[58] Field of Search .............. 585/500, 541, 700, 415, 585/417, 418, 654, 656, 658, 661, 943

[56] References Cited

U.S. PATENT DOCUMENTS

| | | | |
|---|---|---|---|
| 4,205,194 | 5/1980 | Mitchell, III et al. | 585/500 |
| 4,239,658 | 12/1980 | Mitchell, III et al. | 585/500 |
| 4,443,645 | 4/1984 | Jones et al. | 585/500 |
| 4,443,648 | 4/1984 | Jones et al. | 585/500 |

FOREIGN PATENT DOCUMENTS 258608  1/1928  United Kingdom ................ 585/943

OTHER PUBLICATIONS

Keller, G. E., "Synthesis of Ethylene via Oxidative Coupling of Methane", J. of Catalysis, 73, 9–19, (1982).

*Primary Examiner*—William R. Dixon, Jr.
*Assistant Examiner*—Cynthia A. Prezlock
*Attorney, Agent, or Firm*—Craig E. Larson

[57] ABSTRACT

A method is disclosed for converting methane to higher hydrocarbon product by contacting methane with a solid which comprises a reducible metal oxide which when contacted with methane at a temperature within the range of about 500° to 1000° C. is reduced and produces higher hydrocarbon products and a promoting amount of at least one chalcogen component. The preferred chalcogen components are selected from a group consisting of sulfur, selenium, tellurium, and compounds thereof.

19 Claims, No Drawings

METHANE CONVERSION

BACKGROUND OF THE INVENTION

This invention relates to the synthesis of hydrocarbons from a methane source. A particular application of this invention is a method for converting natural gas to more readily transportable material.

A major source of methane is natural gas. Other sources of methane have been considered for fuel supply, e.g., the methane present in coal deposits or formed during mining operations. Relatively small amounts of methane are also produced in various petroleum processes.

The composition of natural gas at the wellhead varies but the major hydrocarbon present is methane. For example, the methane content of natural gas may vary within the range from about 40 to about 95 volume percent. Other constituents of natural gas include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Large scale use of natural gas often requires a sophisticated and extensive pipeline system. Liquefaction has also been employed as a transportation means, but processes for liquefying, transporting, and revaporizing natural gas are complex, energy-intensive and require extensive safety precautions. Transport of natural gas has been a continuing problem in the exploitation of natural gas resources. It would be extremely valuable to be able to convert methane (e.g., natural gas) to more readily handleable or transportable products. Moreover, direct conversion to olefins such as ethylene or propylene would be extremely valuable to the chemical industry.

Recently, it has been discovered that methane may be converted to higher hydrocarbons (e.g., ethane, ethylene and higher homologs) with minimal formation of carbon oxides by contacting methane with a reducible metal oxide as a selective oxygen source. As the methane is converted to hydrocarbon products and coproduct water, the active oxygen of the metal oxide is depleted, resulting in a reduced metal oxide. The reduced metal oxide is relatively inactive for the oxidative conversion of methane but active oxygen may be replaced by regeneration of a reducible metal oxide. Such regeneration is accomplished by reoxidation of the reduced metal oxide.

Reducible oxides of several metals have been identified which are capable of converting methane to higher hydrocarbons. Oxides of manganese, tin, indium, germanium, lead, antimony and bismuth are particularly useful. See commonly-assigned U.S. patent application Ser. Nos. 522,925 (now U.S. Pat. No. 4,443,649); 522,944 (now U.S. Pat. No. 4,444,984); 522,942 (now U.S. Pat. No. 4,443,648); 522,905 (now U.S. Pat. No. 4,443,645); 522,877 (now U.S. Pat. No. 4,443,647); 522,876 (now U.S. Pat. No. 4,443,644); and 522,906 (now U.S. Pat. No. 4,443,646); all filed Aug. 12, 1983, the entire contents of which are incorporated herein by reference.

Commonly-assigned U.S. patent application Ser. No. 522,935, filed Aug. 12, 1983, discloses and claims a process which comprises contacting methane with an oxidative synthesizing agent under elevated pressure (e.g., 2-100 atmospheres) to produce greater amounts of $C_3+$ hydrocarbon products. The entire content of this application is incorporated herein by reference.

Commonly-assigned U.S. patent application Ser. No. 522,938, filed Aug. 12, 1983, discloses and claims a process for the conversion of methane to higher hydrocarbons which comprises contacting methane with particles comprising an oxidative synthesizing agent which particles continuously recirculate between two physically separate zones—a methane contact zone and an oxygen contact zone. The entire content of this application is incorporated herein by reference.

Commonly-assigned U.S. patent application Ser. No. 522,937, filed Aug. 12, 1983, discloses and claims a process for the conversion of methane to higher hydrocarbons which comprises contacting methane with an oxidative synthesizing agent containing a promoting amount of alkali metal and/or compounds thereof. The entire content of this application is incorporated herein by reference.

Commonly-assigned U.S. patent application Ser. No. 522,936, filed Aug. 12, 1983, discloses and claims a process for the conversion of methane to higher hydrocarbons which comprises contacting methane with an oxidative synthesizing agent containing a promoting amount of alkaline earth metal and/or compounds thereof. The entire content of this application is incorporated herein by reference.

Commonly-assigned U.S. patent application Ser. No. 06/600,665 discloses and claims a process for the conversion of methane to higher hydrocarbons which comprises contacting methane with a contact solid comprising a reducible oxide of praseodymium and at least one member of the group consisting of alkali metals, alkaline earth metals, and compounds thereof. The entire content of this application is incorporated herein by reference.

Commonly-assigned U.S. patent application Ser. No. 06/600,918 discloses and claims a process for the conversion of methane to higher hydrocarbons which comprises contacting methane with a contact solid comprising a reducible oxide of terbium and at least one member of the group consisting of alkali metals, alkaline earth metals, and compounds thereof. The entire content of this application is incorporated herein by reference.

Commonly-assigned U.S. patent application Ser. No. 06/600,917 discloses and claims a process for the conversion of methane to higher hydrocarbons which comprises contacting methane with a contact solid comprising a reducible oxide of cerium and at least one member of the group consisting of alkali metals, alkaline earth metals, and compounds thereof. The entire content of this application is incorporated herein by reference.

Commonly-assigned U.S. patent application Ser. No. 06/600,730 discloses and claims a process for the conversion of methane to higher hydrocarbons which comprises contacting methane with a contact solid comprising a reducible oxide of iron and at least one member of the group consisting of alkali metals, alkaline earth metals, and compounds thereof. The entire content of this application is incorporated herein by reference.

Commonly-assigned U.S. patent application Ser. No. 06/600,669 discloses and claims a process for the conversion of methane to higher hydrocarbons which comprises contacting methane with a contact solid comprising a reducible oxide of ruthenium and at least one member of the group consisting of alkali metals, alkaline earth metals, and compounds thereof. The entire content of this application is incorporated herein by reference.

As noted, the reaction products of such processes are mainly ethylene, ethane and other light hydrocarbons, carbon oxides, coke and water. It would be beneficial in these processes to reduce selectivities to carbon oxides and coke and to increase methane conversions to the desired hydrocarbon products.

Accordingly, an object of this invention is to provide an improved process for converting methane to higher hydrocarbons wherein methane is contacted with a reducible metal oxide as a selective oxygen source. A further object of this invention is an improved selective oxygen source—a contact solid capable of enhancing the selective conversion of methane to higher hydrocarbon products. Other aspects, objects and the several advantages of this invention will become apparent to those skilled in the art upon reading this disclosure and the appended claims.

SUMMARY OF THE INVENTION

It has now been found that the method of converting methane to higher hydrocarbons wherein a gas comprising methane is contacted with contact solid comprising a reducible metal oxide may be improved by incorporating a promoting amount of at least one chalcogen component into said contact solid. In one embodiment, the present invention is a method for converting methane to higher hydrocarbon products which comprises contacting a gas comprising methane at a temperature selected within the range of about 500° to 1000° C. with a contact solid which comprises:

(a) at least one reducible oxide of at least one metal which oxide(s) when contacted with methane at said temperature are reduced and produce higher hydrocarbon products and water, and (b) a promoting amount of at least one promoter selected from the group consisting of chalcogens and compounds thereof. Chalcogens are selected from the group consisting of sulfur, selenium and tellurium. Preferred promoters are sulfur, and compounds thereof. Sulfur and compounds thereof are particularly preferred. Reducible oxides of manganese are particularly preferred.

In an alternative embodiment, the present invention is an improved method for converting methane to higher hydrocarbon products comprising contacting a gas comprising methane at a temperature within the range of about 500° to 1000° C. with at least one reducible oxide of at least one metal which oxide(s) when contacted with methane at said temperature are reduced and produce higher hydrocarbon products and water, the improvement which comprises at least periodically contacting a member of the group consisting of said reducible metal oxides, said reduced metal oxides and mixtures thereof with a chalcogen source.

DETAILED DESCRIPTION OF THE INVENTION

In addition to methane the feedstock employed in the method of this invention may contain other hydrocarbon or non-hydrocarbon components. The methane content of the feedstock, however, will typically be within the range of about 40 to 100 vol. %, preferably within the range of about 80 to 100 vol. %, more preferably within the range of about 90 to 100 vol. %.

The solid which is contacted with methane in method of the present process has heretofore been generally referred to as an oxidative synthesizing agent. Oxidative synthesizing agents comprise at least one oxide of at least one metal, which oxides when contacted with methane at temperatures selected within the range of about 500° to 1000° C. produce higher hydrocarbon products, coproduct water and a reduced metal oxide. The composition thus contains at least one reducible oxide of at least one metal. The term "reducible" identifies those oxides of metals which are reduced by the methane contact. The term "oxide(s) of metal(s)" includes: (1) one or more metal oxides (i.e., compounds described by the general formula $M_xO_y$ wherein M is a metal and the subscripts x and y designate the relative atomic proportions of metal and oxide in the composition) and/or (2) one or more oxygen-containing metal compounds, provided that such oxides and compounds have the capability of performing to produce higher hydrocarbon products as set forth herein.

Effective agents for the conversion of methane to higher hydrocarbons have previously been found to comprise reducible oxides of metals selected from the group consisting of manganese, tin, indium, germanium, antimony, lead, bismuth and mixtures thereof.

Reducible oxides of cerium, praseodymium, and terbium have also been found to be effective for the conversion of methane to higher hydrocarbons, particularly when the rare earth component is associated with an alkali or alkaline earth metal component.

Reducible oxides of iron and ruthenium are also effective for the conversion of methane to higher hydrocarbons, particularly when associated with an alkali or alkaline earth metal.

The contact solid (or promoted oxidative synthesizing agent) employed in the process of the present invention contains, in addition to the reducible metal oxide component, at least one chalcogen component. The atomic ratio in which these materials are combined to form the contact solid is not narrowly critical. However, the preferred atomic ratio of the reducible oxide component (expressed as the metal, e.g., Mn) to the chalcogen component (expressed as the chalcogen, e.g., S) may range up to about 1:5, more preferably the ratio is within the range of about 1:3 to 1000:1.

Methane conversion may be improved by introducing a chalcogen source at least periodically into the process. Methane conversion may also be improved by initially using a chalcogen-containing compound to prepare the contact solid. Regardless of how the chalcogen component is introduced into the process, the solid composition will contact such chalcogen, and will retain the chalcogen for a period of time after introduction of the chalcogen is terminated. The retention of the chalcogen and/or the retention of the beneficial effects caused by the presence of the chalcogen is a particularly advantageous feature of the process of this invention.

According to a distinct, highly preferred aspect of this invention, it has been found that the presence of at least one alkali metal component prolongs the period of such retention of the beneficial effects caused by chalcogen addition. Sodium and/or compounds thereof are a particularly preferred alkali metal component of this distinct aspect of the invention.

The contact solid may optionally contain at least one phosphorus component. The amount of phosphorus contained in the contact solid is again not narrowly critical. The atomic ratio of phosphorus to the reducible oxide component (expressed as the metal, e.g., Mn) is preferably less than about 2:1. More preferably, this ratio is within the range of about 0.1–0.5:1.

One preferred contact solid used in the process of this invention may be further expressed by the following empirical formula:

$$A_a B_b P_c O_d$$

wherein A is selected from the group consisting of Mn, Sn, In, Ge, Pb, Sb, Bi and mixtures thereof; B is selected from the group consisting of S, Se, Te and mixtures thereof; a to d indicate the atomic ratio of each component; and when a is 10, b is within the range of about 0.01–30, c is within the range of about 0–20, and d has a value which is determined by the valence and proportions of the other elements present.

The foregoing components of the contact solid may be associated with other support materials such as silica, alumina, titania, magnesia, zirconia and the like and combinations thereof. When employing agents containing rare earth components—oxides of Ce, Pr, and Tb—the rare earth oxides preferably serve as supports.

Reducible oxides of manganese have been found to be particularly desirable for methane conversion according to the method of the present invention. Particularly preferred agents comprise silica- and magnesia-supported, chalcogen-promoted solids containing oxides of manganese and sodium.

The contact solid can be prepared by any suitable method. Conventional methods such as precipitation, coprecipitation, impregnation or dry mixing can be used. Supported solids may be prepared by methods such as adsorption, impregnation, precipitation, coprecipitation, and dry mixing. When phosphorus is incorporated into the agent, it is desirable to provide it in the form of a phosphate of an alkali metal.

A suitable method of preparation is to impregnate a support with solutions of the desired metals. Suitable compounds useful for impregnation include the acetates, acetylacetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solid is calcined, preferably in air, at a temperature within the range of about 300° to 1200° C. Particular calcination temperatures will vary depending upon the particular metal compound or compounds employed.

Chalcogen components may conveniently be incorporated into the contact solid either before or after calcination of the metal-containing composite. A suitable method of incorporation is to impregnate the composite with solutions containing the desired chalcogens. Another suitable method of incorporation is to contact the composite with a chalcogen source.

The chalcogen source may be any of a wide number of materials. The source may be either free chalcogen gas or an chalcogen compound. Suitable sources of chalcogen include hydrogen sulfide, hydrogen selenide, and hydrogen telluride; chalcogen oxides such as $SO_2$; ammonium chalcogenides; aliphatic chalcogenides such as methyl sulfide, methylene sulfide, ethyl sulfide, amyl sulfide and allyl sulfide; cycloaliphatic chalcogenides such as cyclohexyl sulfide; chalcogen substituted aliphatic acids; and organic amine chalcogenide salts; and the like. Mixtures of various chalcogen sources may be used. The presently preferred chalcogen sources are aliphatic chalcogenides, hydrogen chalcogenides, and chalcogen oxides.

Regardless of how the components of the contact solid are combined, the composite will generally be dried and calcined at elevated temperatures prior to use in the process of this invention.

Preferably, methane and oxygen are contacted with the solid in the substantial absence of catalytically effective nickel, noble metals and compounds thereof (i.e., nickel, rhodium, palladium, silver, osmium, iridium, platinum and gold) to minimize the deleterious catalytic effects thereof. These metals, when contacted with methane at the temperatures employed in the method of the present invention, tend to promote coke formation, and the metal oxides tend to promote the formation of combustion products rather than the desired hydrocarbons. The term "catalytically effective" is used herein to identify that quantity of one or more of nickel and of the noble metals and compounds thereof which substantially changes the distribution of products obtained in the method of this invention relative to such contacting in the absence of such metals and compounds thereof.

Operating temperatures for the method of this invention are generally within the range of about 500° to 1000° C. If reducible oxides of metals such as In, Ge or Bi are present in the solid, the particular temperature selected may depend, in part, on the particular reducible metal oxide(s) employed. Thus, reducible oxides of certain metals may require operating temperatures below the upper part of the recited range to minimize sublimation or volatilization of the metals (or compounds thereof) during methane contact. Examples are: (1) reducible oxides of indium, (operating temperatures will preferably not exceed about 850° C.); (2) reducible oxides of germanium (operating temperatures will preferably not exceed about 850° C.); and (3) reducible oxides of bismuth (operating temperatures will preferably not exceed about 850° C.).

Operating pressures for the methane contacting step are not critical to the presently claimed invention. However, both general system pressure and partial pressure of methane have been found to effect overall results. Preferred operating pressures are within the range of about 1 to 100 atmospheres, more preferably within the range of about 1 to 30 atmospheres.

Contacting methane and a reducible metal oxide to form higher hydrocarbons from methane also produces a reduced metal oxide and co-product water. The exact nature of the reduced metal oxides are unknown, and so are referred to herein as "reduced metal oxides". Regeneration of a reducible metal oxide is readily accomplished by contacting such reduced materials with oxygen (e.g., an oxygen-containing gas such as air) at elevated temperatures, preferably at a temperature selected within the range of about 300° to 1200° C., the particular temperature selected depending on the metal(s) included in the solid.

When contacting methane with a promoted contact solid according to the present invention, a single reactor apparatus containing a fixed bed of solids may be used with intermittent or pulsed flow of a first gas comprising methane and a second gas comprising oxygen (e.g., oxygen, oxygen diluted with an inert gas, or air, preferably air). The methane contacting step and the oxygen contacting step may be also performed in physically separate zones with solids recirculating between the two zones.

Thus, a suitable method for synthesizing hydrocarbons from a methane source comprises: (a) contacting a gas comprising methane and a promoted contact solid comprising at least one reducible oxide of at least one metal and a chalcogen promoter to form higher hydrocarbon products, coproduct water, and reduced metal oxide; (b) removing solids comprising reduced metal oxide from the first zone and contacting the reduced solids in a second zone with an oxygen-containing gas to form solids comprising a reducible metal oxide; and (c) returning the contact solid produced in the second zone to the first zone. The steps are preferably repeated at least periodically, and more preferably the steps are continuous. In one more preferred embodiment solids are continuously circulated between at least one methane—contact zone and at least one oxygen-contact zone.

Promoted contact solids comprising a reducible metal oxide which are contacted with methane may be maintained as fluidized, ebullating, or entrained beds of solids. Preferably methane is contacted with a fluidized bed of solids.

Similarly, solids comprising reduced metal oxide which are contacted with oxygen may be maintained as fluidized, ebullating or entrained beds of solids. Preferably oxygen is contacted with a fluidized bed of solids.

In one more preferred embodiment of the present invention, methane feedstock and promoted contact solids are continuously introduced into a methane contact zone maintained at synthesizing conditions. Synthesizing conditions include the temperatures and pressures described above. Gaseous reaction products from the methane contact zone (separated from entrained solid) may be further processed—e.g., they may be passed through a fractionating system wherein the desired hydrocarbon products are separated from unconverted and combustion products. Unconverted methane may be recovered and recycled to the methane contact zone.

Solids comprising reduced metal oxide are contacted with oxygen in an oxygen contact zone for a time sufficient to oxidize at least a portion of the reduced oxide to produce a reducible metal oxide and to remove, i.e., combust, at least a portion of any carbonaceous deposit which may form on the solids in the methane contact zone. The conditions of the oxygen contact zone will preferably include a temperature selected within the range of about 300° to 1200° C., pressures of up to about 30 atmospheres, and average particle contact time within the range of about 1 to 120 minutes. Sufficient oxygen is preferably provided to oxidize all reduced metal oxide to produce a reducible oxide and to completely combust any carbonaceous deposit material desposited on the solids. At least a portion of the promoted contact solids which are produced in the oxygen contact zone are returned to the methane contact zone.

The rate of solids withdrawal from the methane contact zone is desirably balanced with the rate of solids passing from the oxygen contact zone to the methane contact zone so as to maintain a substantially constant inventory of particles in the methane contact zone, thereby enabling steady state operation of the synthesizing system.

When chalcogen-promoted contact solids are employed in the methane conversion process of this invention, it has been found that the enhanced methane conversion activity and selectivity to higher hydrocarbons attributable to the chalcogen component is dissipated over time. Therefore, additional chalcogen component must be incorporated into the contact solid as the cycle is repeated in order to maintain the desirable results obtained by this invention.

It is within the scope of this invention to incorporate additional chalcogen into the contact solid by any of the methods described in the foregoing discussion concerning preparation of the promoted contact solid. Preferably, the solid is periodically contacted with a chalcogen source. Such contact preferably occurs regularly and repeatedly during the cycle comprising methane contact and oxygen regeneration.

For example, when employing a process wherein: (1) a gas comprising methane and solids comprising at least one reducible oxide of at least one metal are continuously introduced and contacted in a first zone (preferably containing a fluidized bed of solids) to produce higher hydrocarbons and (2) an oxygen-containing gas and reduced metal oxides) are contacted in a second zone (also preferably containing a fluidized bed of solids) to regenerate reducible metal oxides); a chalcogen source may be periodically added either to the gas comprising methane being fed to the first zone or to the oxygen-containing gas being fed to the second zone. It is also possible to periodically add the halogen source at least a portion of the solids as they recirculate between the two zones.

When employing a fixed bed reactor system such as that described in U.S. patent application Ser. No. 06/600,143, the entire context of which is incorporated herein by reference, a chalcogen source may be periodically added with: (1) the gas comprising methane, preheated to reaction temperature, as it is introduced to reactors during the methane conversion portion of the fixed bed process cycle; (2) the gas comprising methane as it is being introduced to reactors during the methane preheat portion of the process cycle; (3) the oxygen-containing gas as it is introduced to reactors during the regeneration portion of the process cycle; (4) the purge gas introduced to the reactors between the methane preheat and regeneration portions of the process cycle; and (5) the purge gas introduced to the reactors between the regeneration and methane conversion portions of the process cycle. As will be apparent to one skilled in the art, the process and apparatus disclosed in application Ser. No. 601,143 may also be modified to provide that each reactor is periodically isolated from other process streams and contacted with a chalcogen source.

What is claimed is:

1. In an improved method for converting methane to higher hydrocarbon products wherein a gas comprising methane is contacted at a temperature selected within the range of 500° to 1000° C. with a contact solid comprising at least one reducible oxide of at least metal which oxides when contacted with methane at said temperature are reduced and produce higher hydrocarbon products and water, the improvement which comprises incorporating at least one chalcogen component into said contact solid.

2. A method for converting methane to higher hydrocarbons which comprises:
(a) contacting at a temperature selected within the range of about 500° to 1000° C. a gas comprising methane and a contact solid comprising: (1) at least one reducible oxide of at least one metal selected from the group consisting of Mn, Sn, In, Ge, Pb, Sb and Bi and (2) at least one promoter selected from the group consisting of the chalcogens and compounds thereof, said contacting producing an effluent comprising higher hydrocarbons and water and solids comprising reduced metal oxides;
(b) recovering higher hydrocarbons;
(c) at least periodically contacting solids comprising reduced metal oxides with an oxygen-containing gas to regenerate solids comprising a reducible metal oxide;
(d) at least periodically contacting solids selected from the group consisting of solids comprising reduced metal oxides and said regenerated solids with a chalcogen source to incorporate additional chalcogen promoter into said selected solids; and
(e) contacting a gas comprising methane with solids produced in step (d) as recited in step (a).

3. The method of claim 2 wherein said oxygen-containing gas and said chalcogen source are simultaneously contacted with solids comprising reduced metal oxides.

4. The method of claim 2 wherein said gas comprising methane and said chalcogen source are simultaneously contacted with solids comprising reducible metal oxides.

5. In an improved method for converting methane to higher hydrocarbon products comprising contacting a gas comprising methane at a temperature within the range of about 500° to 1000° C. with at least one reducible oxide of at least one metal which oxide(s) when contacted with methane at said temperature are reduced and produce higher hydrocarbon products and water, the improvement which comprises at least periodically contacting a member of the group consisting of said reducible metal oxides, said reduced metal oxides and mixtures thereof with a chalcogen source.

6. In an improved method for converting methane to higher hydrocarbon products comprising contacting a gas comprising methane at a temperature selected with the range of about 500° to 1000° C. with a solid comprising:
(a) at least one reducible oxide of at least one metal which oxide(s) when contacted with methane at said temperature are reduced and produce higher hydrocarbon products and water; and
(b) at least one member of the group consisting of alkali metals, alkaline earth metals and compounds thereof;
the improvement which comprises at least periodically contacting a member of the group consisting of solids comprising said reducible metal oxides solids comprising said reduced metal oxides and mixtures thereof with a chalcogen source.

7. The method of claim 6 wherein component (b) of the solid is selected from the group consisting of alkali metals and compounds thereof.

8. The method of claim 6 wherein component (b) of the solid is selected from the group consisting of sodium and compounds thereof.

9. The method of claim 6 wherein component (b) of the solid is selected from the group consisting of lithium and compounds thereof.

10. The method of claim 6 wherein component (b) of the solid is selected from the group consisting of potassium and compounds thereof.

11. The method of claim 1 wherein said chalcogen component comprises sulfur and/or a compound thereof.

12. The method of claim 1 wherein said chalcogen component comprises selenium and/or a compound thereof.

13. The method of claim 1 wherein said chalcogen component comprises tellurium and/or a compound thereof.

14. The method of claim 5 wherein said chalcogen component comprises sulfur and/or a compound thereof.

15. The method of claim 5 wherein said chalcogen source comprises selenium and/or a compound thereof.

16. The method of claim 5 wherein said chalcogen source comprises tellurium and/or a compound thereof.

17. The method of claim 7 wherein said chalcogen source comprises sulfur and/or a compound thereof.

18. The method of claim 7 wherein said chalcogen source comprises selenium and/or a compound thereof.

19. The method of claim 7 wherein said chalcogen source comprises tellurium and/or a compound thereof.

* * * * *